(12) United States Patent
Kellie et al.

(10) Patent No.: US 7,061,616 B2
(45) Date of Patent: Jun. 13, 2006

(54) OPTICAL TRANSCEIVER AND METHOD FOR IMAGE DENSITY MEASUREMENT

(75) Inventors: Truman F. Kellie, Lakeland, MN (US); William D. Edwards, New Richmond, WI (US)

(73) Assignee: Samsung Electronics Co., Ltd., Suwon-City (KR)

( * ) Notice: Subject to any disclaimer, the term of this patent is extended or adjusted under 35 U.S.C. 154(b) by 484 days.

(21) Appl. No.: 10/386,858

(22) Filed: Mar. 11, 2003

(65) Prior Publication Data

US 2003/0184756 A1    Oct. 2, 2003

Related U.S. Application Data

(60) Provisional application No. 60/368,233, filed on Mar. 28, 2002.

(51) Int. Cl.
    *G01N 21/55* (2006.01)
(52) U.S. Cl. .................................................. 356/445
(58) Field of Classification Search ............... None
    See application file for complete search history.

(56) References Cited

U.S. PATENT DOCUMENTS

| | | | | |
|---|---|---|---|---|
| 3,869,599 A * | 3/1975 | Sansone | ................ | 235/472.03 |
| 4,054,391 A | 10/1977 | Witte | ......................... | 356/209 |
| 4,155,652 A * | 5/1979 | Buchan et al. | ................ | 399/64 |
| 4,403,406 A | 9/1983 | Foley | ......................... | 29/721 |
| 4,423,736 A * | 1/1984 | DeWitt et al. | .............. | 600/306 |
| 4,472,046 A * | 9/1984 | Kohyama | ....................... | 355/1 |
| 4,502,778 A | 3/1985 | Dodge et al. | ................. | 355/14 |
| 4,587,421 A | 5/1986 | Robertson | ................... | 250/239 |
| 4,603,261 A | 7/1986 | Robertson et al. | .......... | 250/566 |
| 4,696,047 A | 9/1987 | Christian et al. | ............. | 382/8 |
| 4,719,341 A | 1/1988 | Hoogenboom | .............. | 250/201 |
| 4,809,188 A | 2/1989 | Willits et al. | ............... | 364/469 |
| 4,849,784 A | 7/1989 | Blanchet-Fincher et al. | ......................... | 355/274 |
| 4,947,348 A | 8/1990 | Van Arsdell | ................ | 364/523 |
| 4,950,905 A | 8/1990 | Butler et al. | ............. | 250/358.1 |
| 4,989,985 A | 2/1991 | Hubble, III et al. | ........ | 356/445 |
| 5,119,132 A | 6/1992 | Butler | ......................... | 355/208 |
| 5,148,041 A | 9/1992 | Wertheim et al. | ........... | 250/571 |
| 5,240,806 A | 8/1993 | Tang et al. | ................. | 430/115 |
| 5,243,409 A * | 9/1993 | Sagner | ....................... | 356/436 |
| 5,266,803 A | 11/1993 | Heffelfinger | ................ | 250/582 |
| 5,533,139 A | 7/1996 | Parker et al. | ............... | 382/108 |
| 6,043,506 A | 3/2000 | Heffelfinger et al. | ....... | 250/584 |
| 6,061,534 A | 5/2000 | Okada et al. | ................. | 399/51 |
| 6,775,489 B1 * | 8/2004 | Tsuruya et al. | ............... | 399/49 |

FOREIGN PATENT DOCUMENTS

| | | |
|---|---|---|
| EP | 0 574 601 B1 | 9/1998 |
| KR | 57-192978 | * 11/1982 |
| KR | 62-43675 | * 2/1987 |

* cited by examiner

*Primary Examiner*—Michael P. Stafira
(74) *Attorney, Agent, or Firm*—Mark A. Litman & Associates, P.A.

(57) ABSTRACT

An optical transceiver measures optical density of a toned image. The optical transceiver comprises:
a) a bifurcated optical bundle having first and second branches and a common end, each branch having a first plurality of fibers and a second plurality of fibers, respectively, wherein the branches are intermixed in the common end;
b) a radiation source for producing radiation, wherein the radiation source is aligned with the first branch;
c) a detector for detecting the radiation, wherein the detector is aligned with the second branch; and
d) a toner receptor having a surface, wherein the toned image is on the surface and the toner receptor is aligned with the common end.

20 Claims, 2 Drawing Sheets

OPTICAL TRANSCEIVER AND METHOD FOR IMAGE DENSITY MEASUREMENT

This application the benefit of Provisional application Ser. No. 60/368,233, filed Mar. 28, 2002.

BACKGROUND OF THE INVENTION

1. Field of the Invention

This invention relates to a novel optical transceiver for use in measurement, evaluation and correction of optical density of a surface having toned images, more specifically, to the measurement of reflectance of radiation from a toned image surface and to the assignment of correct optical density to the measurement of toned images.

2. Background of the Invention

It is often useful to print large quantities of multi-colored prints to paper for the purpose of disseminating multiple copies of reports or brochure information. One objective of this kind of printing is to assure that all of the reports or brochures look the same, which means that the printing of each of the colors in multi-color pages and the color or shade of black in monochrome pages must maintain a consistent density as printing progresses. It is not desirable to allow the densities of primary colors to vary from page to page because the value and quality of the final product of the reports and/or brochures will be degraded if the colors are varying from document to document. Therefore, measuring density of images (i.e., plated toner) during the printing process is important.

There have been many attempts made to achieve the above objective in the printing process or electrophotographic applications. For example, in U.S. Pat. No. 5,533,139 to Parker et al., a method has been disclosed for detecting coating density imperfections. A light is transmitted through a substrate that is to be inspected, and then significant image processing is applied to make decisions. A quadrifurcated fiber optic bundle has been used with annular illumination techniques so that incident radiation upon the sample is introduced at an angle to the collecting fiber optic axis, as disclosed in U.S. Pat. No. 4,947,348 to Van Arsdell. This disclosure implies that if the surface of the test piece exhibits a large component of specular reflection, then the illuminating radiation will reflect out of the collecting aperture. This kind of annular illumination is good for diffuse surfaces such as paper, but will not work for specular surfaces like polished metal or a photoconductor surface. Moreover, in the disclosed apparatus, all four of the quadrifurcated optical bundle channels are dedicated to detection of radiation and none are used to introduce radiation into the test piece. The annular illuminators are quite large in diameter compared to the fiber bundle and might therefore mechanically interfere with the system being observed.

Another attempt to determine coating density imperfections is disclosed in U.S. Pat. No. 4,950,905 to Butler. This reference uses diffrimoscopic imaging that intentionally throws away directly reflected light and analyzes the diffusely reflected and/or scattered light to make decisions. Not only does this arrangement require a lot of space to set up, but also the signals from diffuse reflection and scattering are weak compared to the specularly reflected component. Consequently this system needs very high quality, high gain amplifiers to function properly.

Bifurcated optical fibers are frequently used in sensors to detect a distance to a target. Typically, one sensor bundle comprises two sets of fibers, each set of fibers originating from a respective branch, the two sets of fibers being joined in a common end. Light is transmitted from a light source through one branch to the target and the corresponding light reflected from the target is conducted by the other branch to a light sensor. The intensity of the reflected light is indicative of the distance between the end of the common branch and the target.

There is a present need for diminutive and inexpensive apparatus and a measurement method capable of indicating the optical density of the toned images on the surface of a substrate, yielding reliable, consistent and accurate results in different applications, including electrophotography.

SUMMARY OF THE INVENTION

In accordance with the invention, there is provided a novel optical transceiver and a method of using the optical transceiver for sensing toner density, particularly plated toner density on the surface of a toner receptor.

In a first aspect, the invention features an optical transceiver that includes: (a) an at least bifurcated optical bundle having at least a first branch and a second branch and a common end, each of the first branch and second branch having a first plurality of fibers and a second plurality of fibers respectively, wherein the branches are combined or each set of plurality of fibers are intermixed in the common end; (b) a radiation source for producing or providing radiation, wherein the radiation source is aligned with the first branch to allow radiation to enter into and be carried by the first branch; (c) a detector for detecting the radiation, wherein the detector is aligned with the second branch to receive radiation transmitted by the second branch; and (d) a toner receptor having a surface, wherein a toned image is on the surface of the toner receptor and the toner receptor is optically aligned with the common end. The term optical alignment refers to the physical arrangement whereby light or radiation reflected from the surface of the toner receptor can enter into optical openings on the second branch. The orientation must be within a ±90° orientation to the surface, and preferably is within a ±45° orientation with respect to fibers being directly aimed at or perpendicular to the plane of the surface, more preferably within a ±30° orientation and within a ±20° orientation, or within a ±10° orientation towards the surface.

In a second aspect, the invention features a method for measuring optical density of a toned image that includes: (a) providing radiation from a radiation source, wherein the radiation has stable intensity (e.g., by stable intensity it is meant that the energy at a wavelength or range of wavelengths, including white light, does not vary more than ±5% in energy/fluence during a measurement period, preferably not more than 3%, and more preferably less than or equal to 2% or less than or equal to 1%); (b) providing an at least bifurcated optical bundle having first and second branches and a common end, each branch having a first plurality of fibers and a second plurality of fibers respectively, wherein the branches are intermixed in the common end; (c) aligning the common end with a toner receptor having a surface (e.g., as with the alignment above, the range of orientations should be within the same ranges described above, most preferably within a ±20° orientation, or within a ±10° orientation towards the surface as measured from a line perpendicular to the plane of that surface), wherein the toned image is on the surface; (d) emitting the radiation from the radiation source through the first branch and the common end to the surface; (e) receiving radiation reflected from the surface through the common end to the second branch by a detector, wherein the detector generates an electrical signal depending upon the intensity of the reflected radiation; (f) providing means to move the toned surface with respect to the common end; (g) generating and storing a color specific look up table by evaluating density in a test patch of plated toner on the toner receptor; (h) adjusting imaging process parameters in a process used to generate a toned image in accordance to values in a look up table; and (i) preferably repeating the above procedures for at least one more color and preferably each color of a multi-color printing process.

In a third aspect, the invention features an optical transceiver that includes: (a) an at least bifurcated optical bundle having at least first branch and second branch and a common end, each of the first branch and second branch having a first plurality of fibers and a second plurality of fibers respectively, wherein the plurality of the fibers in each branch or each of the branches are intermixed in the common end; (b) a radiation source for producing radiation, wherein the radiation source is aligned with the first branch to allow radiation to enter into and be carried by the first branch; (c) a detector for detecting the radiation, wherein the detector is aligned with the second branch to receive radiation transmitted by the second branch; (d) a toner receptor having a surface, wherein the toned image is on the surface and the toner receptor is aligned with the common end; and (e) a microprocessor for receiving and storing radiation data from the detector and for determining the position of the common end with respect to the toner receptor. It is to be noted that the intermixing of the fibers from each of the branches may be done so as to form a distinct and highly efficient distribution of both sets of fibers so as to maximize relative transmission from the first bundle (branch) to be reflected and carried by the second bundle (branch). For example, the fibers of the first branch may be distributed at the common end in concentric circles, in a circular distribution that defines the perimeter of all fibers in the common end or in a single core of fibers. In cooperation with that distribution, the fibers of the second branch may be distributed in concentric circles intermediate or adjacent to concentric circles of fibers from the first branch, fibers from the second branch may form a core within the perimeter defined by first branch fibers, or may themselves define a perimeter around a core of fibers from the first branch. It is also possible to have fibers from the first branch and fibers from the second branch evenly distributed within the common end, either in a defined pattern or a more approximately even distribution. These more designed mixtures of fibers will assist in maximizing return of light from the first branch back into fibers in the second branch after reflection from the surface.

These and other aspects, advantages and features of the present invention will be more readily understood from the following detailed description of certain preferred embodiments thereof, when considered in conjunction with the appended claims and the drawings hereto.

DETAILED DESCRIPTION OF THE INVENTION

While the present invention will hereinafter be described in connection with one or more preferred embodiments thereof, it will be understood that it is not intended to limit the invention to that embodiment. On the contrary, it is intended to cover all alternatives, modifications and equivalents as may be included within the spirit and scope of the invention as defined by the appended claims.

Figure 1:
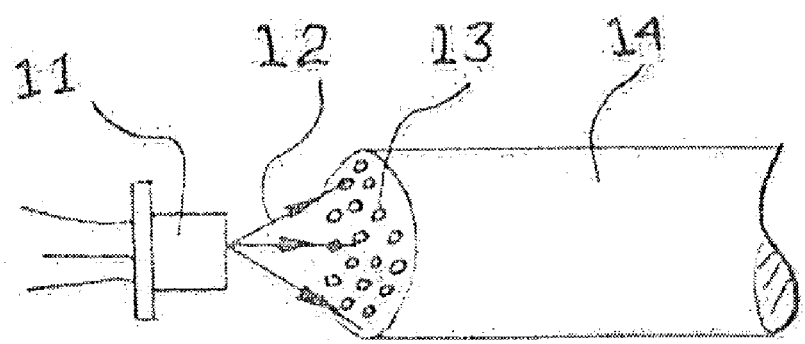
FIG. 1 is a partial schematic diagram depicting the input portion of an optical transceiver pursuant to the present invention, consisting of a radiation source and a first branch of the bifurcated optical bundle.

Referring now to FIG. 1, radiation source 11 may be any of a variety of source types and wavelengths such as light emitting diode (UV, infrared, red, or other visible radiation wavelengths), laser, continuously tunable broadband source, or even incoherent white light. Radiation 12 is emitted from radiation source 11. While the output intensity of radiation 12 may be controlled by neutral density filters or by electronic intensity controllers controlling the power supply for radiation source 11, preferably the radiation is a stable radiation such that the intensity and the wavelength of the radiation varying less than 1% over several hours of printing operations. This stability may also be required during the life of printer, measuring energy intensity such as might be achieved by using the output signal from a laser diode internal detector to servo the forward current to the junction. In one embodiment of the present invention, radiation source 11 may be a solid state laser diode such as Model LT080MD, commercially available from Sharp Corporation, Mahwah, N.J.

Figure 2:
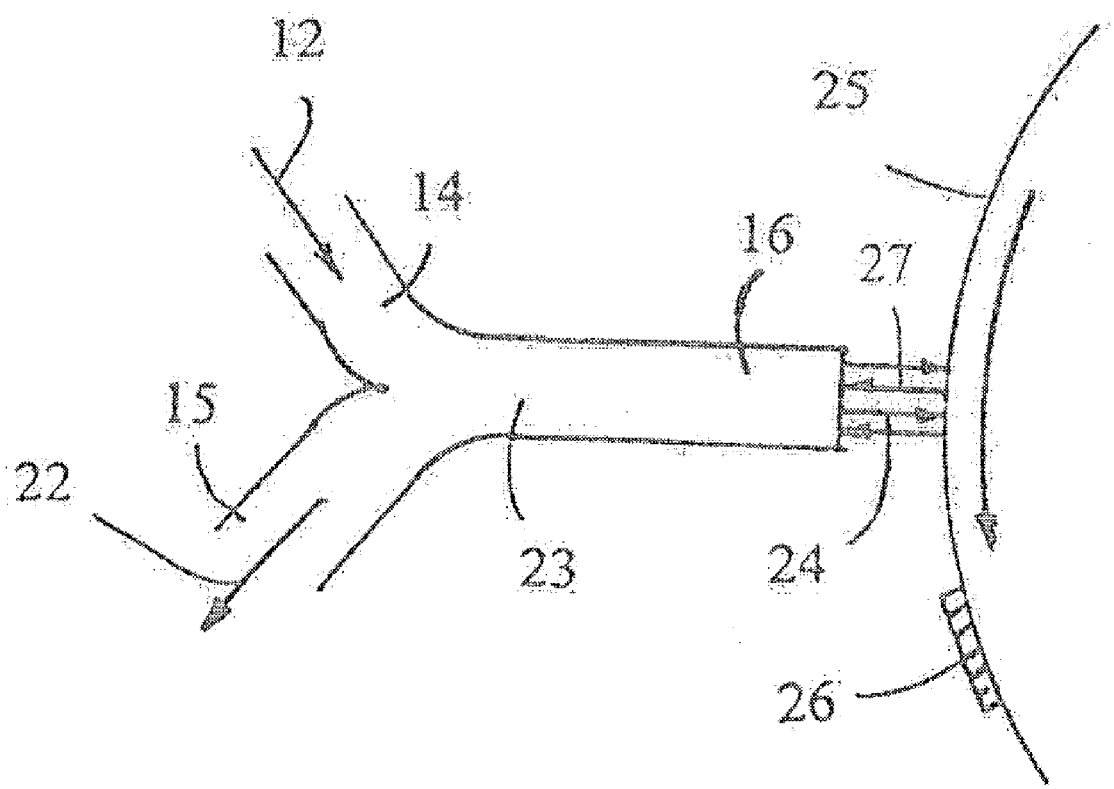
FIG. 2 is a partial schematic diagram of a toner receptor and the bifurcated optical bundle of an optical transceiver pursuant to the present invention.

Referring to FIG. 2, first branch 14 shown is a part of bifurcated optical bundle 23 at the distal side of the bundle. Bifurcated optical bundle 23 may be any commercially available optical fiber bundle, composed of small individual optical fibers 13. Bifurcated optical bundle 23 comprises first branch 14 and second branch 15 which join together at common end 16. In a preferred embodiment of the present invention, bifurcated optical bundle 23 is a Model BMP 753P, commercially available from Banner Engineering Corp., Minneapolis, Minn. Radiation source 11 is by definition properly or appropriately aligned with first branch 14 when a percentage of photons (e.g., greater than 50%) approaching the maximum number of photons leaving the source are fired successfully into the end of the fiber bundle first branch 14. This can be realized most easily by detecting photons radiating from the common end with a detector and maximizing the signal from that detector by properly adjusting the relationship between the radiation source and the fiber bundle. Radiation 12 is then emitted from radiation source 11 and collected by fibers in first branch 14. In order to achieve stable, reliable and repeatable results the alignment of first branch 14 with radiation source 11 must be strictly maintained during testing.

FIG. 2 also depicts the geometric alignment of toner receptor 25 and common end 16 of bifurcated optical bundle 23 of the optical transceiver in accordance with an aspect of the invention. Toned image 26 is deposited on the surface of toner receptor 25. Suitable materials for toner receptor 25 include but are not limited to paper, metal, metal coated substrates, composites, photoreceptors and the like. Toner receptor 25 can be in the form of sheet, roll, drum, disk, or belt. Furthermore, in electrophotographic applications, toner receptor 25 may be a developer roll, an intermediate transfer member, a photoreceptor, or a receiving medium such as paper.

In a preferred embodiment, toner receptor 25 is a photoreceptor. A photoreceptor may be in the form of a plate, belt, or roll (i.e., drum). A photoreceptor has an electrically insulating photoconductive element on an electrically conductive substrate and is imaged by first uniformly electrostatically charging the surface of the photoconductive element, and then exposing the charged surface to a pattern of light. The light exposure selectively dissipates the charge in the illuminated areas, thereby forming a pattern of charged and uncharged areas. A liquid or solid toner is then deposited in either the charged or uncharged areas to create a toner receptor on the surface of the photoconductive element. The resulting visible toned image can be fixed to the photoreceptor surface or transferred to the surface of the suitable receiving medium. The imaging process can be repeated many times on the reusable photoconductive element.

As briefly described above, bifurcated optical bundle 23 (a bifurcated bundle is a bundle in which two separate sources of fibers are combined) includes first branch 14 and second branch 15 and common end 16, in which only the common end has the first and second plurality respectively of intermixed fibers, in which the fibers are combined from both first branch 14 and second branch 15 without any spatial ordering. The fibers may be segregated by function when intermixed (e.g., distributed in a specific pattern after combination, such as alternating functions, groups of fibers in an alternating association of functions, or may be randomly distributed in the mixture.) The structures are within the control and design of the manufacturer, and preferred orientations as individual fibers or as groups of fibers are described above. Radiation 12 received by the input portion of the optical transceiver propagates through first branch 14 and then to common end 16 of the bifurcated optical bundle 23. Common end 16 is placed directing radiation to and aligned properly with toner receptor 25. Common end 16 is by definition aligned properly to toner receptor 25 when common end 16 is approximately (e.g., within plus-or-minus ten degrees from a line perpendicular to the central point of impact of radiation 24 on the surface 25) of perpendicular to toner receptor 25 with a standoff distance adjusted to within ten and preferably within five millimeters (e.g., approximately three or four millimeters) so that an approximately maximum signal is obtained by the detector. Toner receptor 25 bearing toned image 26 on its surface is then relatively translated (along at least one dimension as with rotation of the toner receptor and preferably along two dimensions of length and width) with respect to common end 16 to produce measurement data. This translation may be in a raster fashion or any other pattern of movement that covers the entire imaged area of the surface. The two dimensions may be effected by moving the common end 16 in two dimensions or by moving the common end in one dimension perpendicular or at an angle away from the dimension of movement of the toner surface 25 at the point where it is impacted by radiation 24.

A preferred embodiment is where the toner receptor 25 is a photoreceptor roll illuminated with radiation 24, which illuminating radiation is derived from radiation 12 that exits from common end 16. The wavelength of radiation 12 and thus radiation 24 is selected such that radiation 24 is transmissible in the form of a toned image 26 but with at least some small amount of absorption by the toner. For most colored toners, a light emitting diode or solid state laser diode used in this preferred embodiment of the invention produces a satisfactory wavelength of light for this purpose in the near infrared range, although a specific toner may be non-absorbing to other wavelengths of light. Radiation 24 passed through toned image 26 is reflected from the surface of toner receptor 25. As the surface of toner receptor 25 (e.g., a photoreceptor) rotates such as by means of a DC motor or a stepper motor, the intensity of the specularly reflected radiation 27 varies in proportion to the thickness of toned image 26. One of the advantages of bifurcated optical bundle 23 in the present invention is the diminutive size of common end 16. That is, bifurcated optical bundle 23 allows one to design a small-sized probe of the interface in common end 16 and to place it in any area to be measured, which lowers the cost and broadens the applications of the present invention. Because variation of standoff distance between the common end of the bifurcated bundle and the toner receptor may adversely affect the density measurement, it is advisable to place this measurement system over a back up roll (in the case of a flexible toner receptor), but the system is not disadvantaged by any curvature of the toner receptor surface at the point of measurement. Similar to the importance of mechanical stability of the alignment described above, the stability of common end 16 is needed for obtaining reliable and repeatable results during the measurement. As used herein, specular reflection refers to that portion of reflected radiation wherein the angle of reflection is equal to the angle of incidence. For example, collimated incident radiation may be reflected as an angular distribution which is sharply peaked about the specular reflection angle. This would be considered to be specularly reflected. Specularly reflected radiation 27 from the surface of toner receptor 25 passes through toned image 26 and reenters common end 16 of bifurcated optical bundle 23. A non-limiting example of the usefulness of specular reflection technique in the present invention is its broad applications, i.e., the technique may be used for surfaces that even exhibit a large amount of specular reflection, such as a polished surface. Specularly reflected radiation 27 propagates to second branch 15 of bifurcated optical bundle 23 and comes out as radiation 22.

Figure 3:
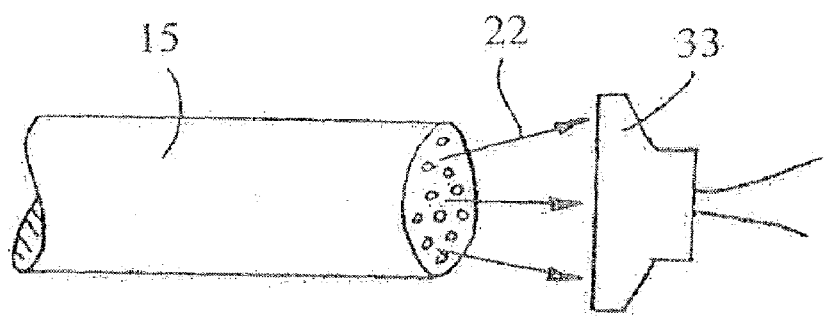
FIG. 3 is a partial schematic diagram showing an arrangement that constitutes the detection portion of an optical transceiver pursuant to the present invention, consisting of a second branch of the bifurcated optical bundle and a detector.

FIG. 3 shows an arrangement that constitutes a detection portion according to a practice of the present invention. Detector 33 receives radiation 22 propagated from second branch 15 of bifurcated optical bundle 23. Detector 33 may be any sensor that can quantitatively and/or qualitatively detect and provide relative measurements of radiation, such as a photo transistor, a photomultiplier tube, or the like. One preferred detector for this invention is a photodiode, Model L54-034, commercially available from Edmund Industrial Optics, Barrington, N.J. The Second branch 15 of bifurcated optical bundle 23 is positioned such that substantially all the radiation exiting from the end of the bundle is collected by the detector 33 in order to obtain the maximum signal-to-noise ratio. In this arrangement, the mechanical stability described above has to be considered as well.

Figure 4:
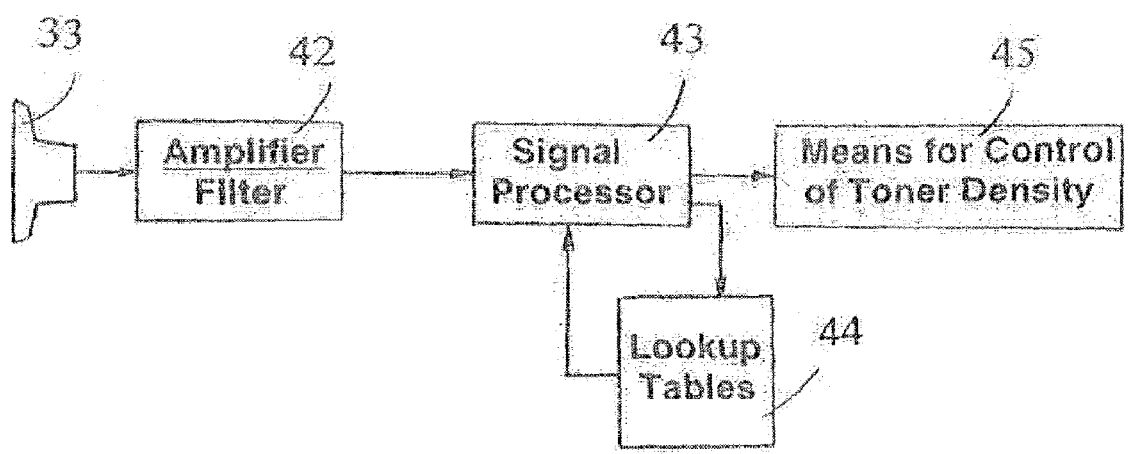
FIG. 4 is a schematic block diagram of a process of generating a digital output value pursuant to the present invention

FIG. 4 is a block diagram showing an analog electrical signal from detector 33 being processed and compared to look up table 44 values containing calibration information to yield a digital output that is directly proportional to the toner film thickness of the test sample being measured. A calibration procedure to generate and store look up table 44, with given test sample (e.g., test patch) is described in an elaborated way below. The analog electrical signal from detector 33 is amplified and filtered by amplifier module 42, and then processed as required by signal processor 43 which uses lookup table 44, generated from a calibration procedure. The result of the processing yields a digital output value which actually indicates the optical density of toned image 26.

When the optical transceiver has been assembled according to the above outlined procedure and properly aligned with respect to radiation source 11, detector 33 and toner receptor 25 according to the procedure outlined above, it is of interest to generate a specific relationship between the output of detector 33 located near second branch 15, i.e., the proximal end of bifurcated optical bundle 23 and the density of a test patch of plated toner on toner receptor 25. The calibration procedure is described in the following way.

The baseline of digital output value is recorded when there is no toner on toner receptor 25 to provide a base or 'white' background density for the receptor. This value may be assumed or actually measured, but it is preferred to actually record a measured value. For the purpose of obtaining an extremely accurate value in the absence of any toner, the surface of toner receptor may be rotated for several revolutions and the average value of the digital output value is calculated and stored for use as a baseline of zero density. If the standard deviation of the average value of the digital output value is greater than a specifically defined amount such as 2% of the average value, then toner receptor 25 is seen to have variable reflection as a function of angular position and a table (lookup table) may be constructed for the recording of the digital output value as a function of angular position. If the extent of the toner patch to be measured is several angular degrees of rotation of toner receptor 25, then a look up table of values should have an entry for zero density for every several angular degrees and the position of the toner test patch to be measured must be known so that the correct value of zero density may be chosen to calculate the correct density of the toner patch. A microprocessor or computer associated with the system translating the toner receptor provides the information on the angular position on the test patch and an actual image during operation of the system. If the standard deviation of the average value of the digital output value is less than, for example, 2% of the average value, then one global value (the average value) for zero density may be stored and used for all density calculations, regardless of the angular position of the toner test patch on toner receptor. With the measurement system in place and the zero density value determined, a toner test patch of known density may be printed on the toner receptor and the digital output value recorded as the toner patch is made to pass before the distal end of the bifurcated optical fiber bundle 23, i.e., common end 16. A next step is to repeat the process several times for several density values of the toner patch. The range of density values that are recorded and measured in this way should include at least the target density for the particular color being printed. The data collected in the above steps may be assembled into a lookup table for use by the printer CPU during printing to measure toner test patches and adjust operation process parameters, e.g., voltage bias, force, development gap, etc. in electophotographic application (EP parameters), in a printing machine to maintain the desired density for a particular color.

In the case of printing of multiple colors, each color would need a separate optical transceiver and a separate lookup table in order to adequately control the multicolor printing of constant densities.

The above process can also be used in an optical transceiver of the present invention for measuring and thereby controlling the optical density of toned images. The digital output value may enter into any system or component that can control toner density 45 wherein operation parameters of an apparatus are modulated for consistent optical density of toned images, using control schemes, e.g., feed-back control. For example, in an electrophotographic application, electrophotography process parameters such as applying voltage or amount of toners supplied can be controlled for consistent optical density of toned images during the printing process.

Although several embodiments of the present invention have been illustrated in the accompanying drawings and described in the foregoing detailed description, it will be understood that the invention is not limited to the particular embodiments described herein, but is capable of numerous rearrangements, modifications and substitutions without departing from the scope of the invention.

Other enabled embodiments are described within the following claims.

What is claimed is:

1. An optical transceiver for measuring optical density of a toned image, said optical transceiver comprising:
   a) an at least bifurcated optical bundle having at least a first branch and a second branch and a common end, each of said first and second branches having a first plurality of fibers and a second plurality of fibers, respectively, wherein fibers from said first branch and fibers from said second branch are intermixed in said common end;
   b) a source of radiation, wherein said radiation source is optically aligned with said first branch;
   c) a detector for detecting said radiation and providing data to a processor, wherein said detector is optically aligned with said second branch; and
   d) a toner receptor having a surface,
   wherein said toned image is on said surface and said toner receptor is optically aligned with said common end and the processor using a color specific look up table to evaluating density in plated toner on said toner receptor.

2. An optical transceiver according to claim 1, further comprising a system that moves said surface with respect to said common end.

3. An optical transceiver according to claim 1, wherein said radiation source comprises a light emitting diode.

4. An optical transceiver according to claim 1, wherein said radiation source comprises a solid state laser diode.

5. An optical transceiver according to claim 1, wherein said radiation source comprises a white light source.

6. An optical transceiver according to claim 1, wherein said detector comprises a photodiode.

7. An optical transceiver according to claim 1, wherein said detector comprises a phototransistor.

8. An optical transceiver according to claim 1, wherein said detector comprises a photomultiplier tube.

9. An optical transceiver according to claim 1, wherein said toner receptor comprises a photoreceptor.

10. An optical transceiver according to claim 1, wherein said toner receptor comprises an intermediate transfer member.

11. An optical transceiver according to claim 1, wherein said toner receptor according to claim 1, wherein said toner receptor comprises a paper.

12. An optical transceiver according to claim 1, wherein said toner receptor comprises a roll.

13. An optical transceiver according to claim 12, wherein said roll is a developer roll.

14. An optical transceiver according to claim 12, wherein said roll further comprises a photoreceptor.

15. An optical transceiver according to claim 1, wherein said toned image is a color image.

16. The optical transceiver of claim 1 wherein optical fibers from the first branch and the second branch are arranged in a circular pattern in said common end.

17. The optical transceiver of claim 13 wherein optical fibers from the first branch and the second branch are arranged in a circular pattern in said common end.

18. A method for measuring optical density of a toned image, said method comprising the steps of:
   a) providing radiation from a radiation source, wherein said radiation has stable intensity;
   b) providing an at least bifurcated optical bundle having at least a first branch and a second branch of fibers and a common end, each branch of fibers having a first plurality of fibers and a second plurality of fibers, respectively, wherein said branches are intermixed in said common end;
   c) optically aligning said common end with a toner receptor having a surface, wherein said toned image is on said surface;
   d) emitting said radiation from said radiation source through said first branch and out of said common end to said surface;
   e) receiving radiation reflected from said surface into fibers in the second branch by a detector, wherein said detector generates an electrical signal depending upon the intensity of radiation detected
   f) moving the toned surface with respect to said common end;
   g) generating and storing a color specific look up table by evaluating density in a test patch of plated toner on said toner receptor;
   h) adjusting imaging process parameters in a process used to generate a toned image in accordance to values at look up table.

19. A method for measuring optical density of a toned image, said method comprising the steps of:
   a) providing radiation from a radiation source, wherein said radiation has stable intensity;
   b) providing an at least bifurcated optical bundle having at least a first branch and a second branch of fibers and a common end, each branch of fibers having a first plurality of fibers and a second plurality of fibers, respectively, wherein said branches are intermixed in said common end;
   c) optically aligning said common end with a toner receptor having a surface, wherein said toned image is on said surface;
   d) emitting said radiation from said radiation source through said first branch and out of said common end to said surface;
   e) receiving radiation reflected from said surface into fibers in the second branch by a detector, wherein said detector generates an electrical signal depending upon the intensity of radiation detected
   f) moving the toned surface with respect to said common end;
   g) generating and storing a color specific look up table by evaluating density in a test patch of plated toner on said toner receptor;
   h) adjusting imaging process parameters in a process used to generate a toned image in accordance to values at look up table, wherein steps d) through h) are repeated for each color of multi-color printing process.

20. An optical transceiver for measuring optical density of a toned image, said optical transceiver comprising:
   a) an optical bundle having at least a first branch and a second branch of optical fibers and a common end, each of the first branch and the second branch having a first plurality of optical fibers and a second plurality of optical fibers, respectively, wherein optical fibers from the first branch and the second branch are distributed across a cross-section of the common end;
   b) a radiation source, wherein said radiation source is optically aligned with the first branch and transmitted through said first branch;
   c) a detector for detecting said radiation, wherein said detector is optically aligned with the second branch and receives radiation from said second branch;
   d) a toner receptor having a surface, wherein said toned image is on said toner receptor surface and said toner receptor is optically aligned with said common end; and
   e) a microprocessor for receiving and storing radiation data from said detector and for determining the position of said common end with respect to said toner receptor.

* * * * *